United States Patent
Reyneke et al.

(10) Patent No.: US 7,437,891 B2
(45) Date of Patent: Oct. 21, 2008

(54) RECOVERY AND PURIFICATION OF ETHYLENE

(75) Inventors: Rian Reyneke, Katy, TX (US); Michael J. Foral, Aurora, IL (US); Guang-Chung Lee, Houston, TX (US); Wayne W. Y. Eng, League City, TX (US); Iain Sinclair, Warrington (GB); Jeffery S. Lodgson, Naperville, IL (US)

(73) Assignee: Ineos USA LLC, Lisle, IL (US)

( * ) Notice: Subject to any disclaimer, the term of this patent is extended or adjusted under 35 U.S.C. 154(b) by 587 days.

(21) Appl. No.: 11/017,159

(22) Filed: Dec. 20, 2004

(65) Prior Publication Data

US 2006/0135840 A1    Jun. 22, 2006

(51) Int. Cl.
*F25J 3/02* (2006.01)
*B01D 3/00* (2006.01)
*C10G 7/00* (2006.01)
*C07C 7/00* (2006.01)
*C07C 7/04* (2006.01)

(52) U.S. Cl. .............................. 62/935; 62/620; 62/622; 62/623; 62/627; 62/932; 208/350; 208/351; 208/353; 208/355; 585/809

(58) Field of Classification Search ................. 62/607, 62/620, 622, 623, 627, 931, 932, 935, 939; 208/347, 350, 353, 355, 351; 585/800, 809
See application file for complete search history.

(56) References Cited

U.S. PATENT DOCUMENTS

| 5,675,054 | A | 10/1997 | Manley | ...................... 585/809 |
| 5,746,066 | A | 5/1998 | Manley | ...................... 62/612 |
| 6,212,905 | B1 | 4/2001 | Kuechler et al. | .............. 62/630 |
| 2004/0182751 | A1 | 9/2004 | Reyneke et al. | ............. 208/351 |
| 2005/0154245 | A1* | 7/2005 | Reyneke et al. | ............. 585/800 |

OTHER PUBLICATIONS

Heinz Zimmerman & Roland Walzl, "Ethylene" in: Ullman's Encyclopedia of Industrial Chemistry (2007 ed.), vol. A10, pp. 1, 2, 5-9, and 33-41.*

* cited by examiner

*Primary Examiner*—Glenn Caldarola
*Assistant Examiner*—Randy Boyer
(74) *Attorney, Agent, or Firm*—David P. Yusko; James J. Drake

(57) ABSTRACT

A process for the recovery and purification of ethylene and optionally propylene from a stream containing lighter and heavier components that employs an ethylene distributor column and a partially thermally coupled distributed distillation system.

31 Claims, 2 Drawing Sheets

RECOVERY AND PURIFICATION OF ETHYLENE

STATEMENT REGARDING FEDERALLY SPONSORED RESEARCH OR DEVELOPMENT

This invention was made with government support under United States Department of Energy Cooperative Agreement No. DE-FC07-01ID 14090.

BACKGROUND OF THE INVENTION

1. Field of the Invention

This invention relates to the recovery and purification of ethylene and optionally propylene from a multi-component gas mixture which contains components that are both lighter and heavier than the olefins that are to be recovered and purified, and more particularly relates to the recovery of ethylene and optionally propylene from the cooled effluent of a steam cracking furnace by a process employing an ethylene distributor column.

2. Discussion of the Prior Art

The method of the present invention can be employed generally for recovering and purifying ethylene and optionally propylene but is described herein in the context of recovering and purifying ethylene and optionally propylene from the effluent of a steam cracking furnace. In a typical ethylene manufacturing plant, hydrocarbon feeds are vaporized if necessary, preheated, mixed with steam, and directed to a steam cracking furnace. Many different kinds of hydrocarbon feeds can be used, including ethane, propane, butane, naphthas, distillates, and gas oils. Mixtures of hydrocarbons can also be used, but because the optimum furnace conditions for each feed type vary, it is preferable that different hydrocarbons be segregated and cracked in different furnaces.

In a steam cracking furnace the relatively low-pressure hydrocarbon and steam mixture is subjected to high temperatures which convert the hydrocarbon into a furnace effluent gas mixture, typically comprising ethylene, methane, hydrogen and unconverted feed, as well as some hydrocarbons heavier than the feed. The hot furnace effluent gas is cooled by raising high pressure steam and also typically by direct contact with circulated cooled quench oil and/or circulated cooled water. These cooling steps typically condense and at least partially remove relatively heavy hydrocarbons, typically in the naphtha range and heavier.

The uncondensed cooled effluent gas is then directed to a compressor section in which the gas is compressed in one or more stages (typically 3-5 stages) to an elevated pressure. The effluent from each stage is typically cooled against an ambient temperature medium and any condensed liquids removed before entering the subsequent compression stage. Acid gases such as $H_2S$ and $CO_2$ are generally removed after one of these stages of compression, for example through the use of a caustic contacting tower or an amine scrubbing system. Once compressed, scrubbed and dried, the furnace effluent gas enters the separation section.

A typical ethylene plant separation section employs a number of distillation towers for the purpose of recovering ethylene from the furnace effluent gas and purifying it sufficiently for use in downstream processes, such as the manufacture of polyethylene. A number of alternatives exist for the design of the ethylene separation section. Typically ethylene separation designs will employ at least a deethanizer tower which has the purpose of separating C2 and C3 components (that is, ethylene and ethane from propylene and propane, respectively), a demethanizer tower for separating C2 components from any components lighter than the C2s, and a C2 splitter for the final separation of ethylene from ethane.

The use of distillation to purify products from olefins plants is well known in the art. Conventional distillation schemes typically have utilized "sharp-split" distillation, wherein each distillation column is used to make a sharp separation between adjacent components of a homologous series. In a sharp-split distillation sequence, each component leaves the distillation column in a single product stream, either as overheads or bottoms. An inherent inefficiency in sharp-split distillation can be observed by considering the number of phase changes necessary to produce a recoverable hydrocarbon component. For example, a hydrocarbon gas feed typically containing C1+ hydrocarbons, such as ethylene, is first condensed in a demethanizer, then revaporized in a deethanizer, and is finally condensed again as a liquid product from a C2 splitter. A total of three complete phase changes must be accomplished for all the ethylene. The same number of phase changes applies to ethane and propylene.

The energy required to recovery and purify a hydrocarbon component such as ethylene can be reduced by utilizing a refinement upon conventional, sharp-split distillation. Such a refinement is known as distributed distillation. Such schemes require less energy to operate than conventional sharp-split schemes. In distributed distillation schemes, sharp cuts are not necessarily made between components. Instead, one or more of the components is "distributed" between the top and bottom of one or more distillation columns. This results in energy savings in part because the total number of phase changes necessary to produce ethylene product is reduced compared with a sharp split flowsheet, and the thermodynamic efficiency of the process is therefore improved. In addition, distributed distillation provides additional degrees of freedom for energy optimization—namely, the distribution ratio of the distributing components in each column.

The present invention also relates to the use of an ethylene distributor column for the recovery and purification of ethylene. For the purpose of this invention, an ethylene distributor column is one in which a sharp split is made between components lighter than ethylene and components heavier than ethylene. Therefore the ethylene distributor overhead stream contains ethylene and any components lighter than ethylene that enter the ethylene distributor. In particular, the ethylene distributor overheads contain a sufficiently low concentration of ethane that no further ethane/ethylene separation is needed in order to produce a purified ethylene product from this stream. The ethylene distributor bottoms stream contains ethylene and any components heavier than ethylene that enter the ethylene distributor.

Additional energy savings can be gained by thermally coupling (also called recycle-coupling) columns such that all or at least part of the stripping vapor or reflux liquid of a column is provided by a vapor or liquid side-draw from a downstream tower. Furthermore, the use of a mixed refrigerant system to provide the required coldest level refrigeration requirements would further reduce the energy requirement of such a separation system. Examples of a completely thermally coupled distributed distillation system have been disclosed in Manley et al., U.S. Pat. Nos. 5,675,054 and 5,746,066, which disclose the use of an ethylene distributor column and a mixed refrigeration system in a complete thermally coupled distributed distillation system. Both patents disclose thermally coupled embodiments for ethylene separation, including an embodiment that recites a front-end depropanizer ethylene recovery and purification process that utilizes full thermal coupling of the C2s distributor, deethanizer, demethanizer, ethylene distributor, and C2 splitter columns. The thermal coupling of the columns is integral to the claimed energy efficiency of this prior art process.

All of the columns recited in Manley's embodiments operate at substantially the same pressure, with any differences in pressure due to typical hydraulic pressure drops through the columns, exchangers, and piping. Substantial differences in pressure between the columns would require vapor compression or liquid pumping between columns. Manley recites that such a fully-coupled distributed distillation system has lower energy requirements than systems that are not thermally coupled. Conventional wisdom also suggests that such an arrangement, being fully thermally coupled, would be more energy efficient than a scheme that has no couples or is only partially thermally coupled.

Furthermore, neither of these patents discloses a separation of hydrogen and methane intermediate between the ethylene distributor tower and the demethanizer tower, which would be beneficial for increasing the recovery of hydrogen to salable product. It could also be beneficial from both the energy and operability standpoint to replace some of the thermal coupling with, for example, a standard reboiler to provide stripping vapor to the ethylene distributor.

However, while a completely thermally coupled arrangement would require the lowest overall heating and cooling duty, it does not necessarily represent the lowest energy solution when the refrigeration compression energy required to service the sub-ambient duties is considered. By considering these additional design aspects we have discovered, surprisingly, a partially coupled scheme that is actually more energy efficient than the fully-coupled scheme described by Manley. In particular, two of the thermal couples taught by Manley et al., specifically the thermal couple between the C2 distributor and deethanizer columns and the thermal couple between the ethylene distributor and the deethanizer or C2 splitter, actually increase the energy requirement for the process when implemented in a conventional cracker with conventional vapor recompression refrigeration systems. The distillation system of this invention, therefore, does not include these couples and represents an unexpected improvement in energy savings as compared to Manley et al. In addition, it has been found that removing these two thermal couples allows the deethanizer and/or C2 splitter to be operated at a lower, more optimal pressure than the rest of the distillation sequence. The full thermal coupling recited by Manley et al., on the other hand, requires that all columns be operated at roughly the same pressure, or utilize energy intensive vapor compression between columns. A partially coupled scheme can also be an improvement from any operability standpoint relative to a fully thermally coupled scheme.

Another disclosure of the use of an ethylene distributor is in Kuechler et al., U.S. Pat. No. 6,212,905, which teaches a process in which a secondary ethylene product stream is recovered from a mixed gas stream at a temperature higher than −55° F. The patent does not disclose a separation of ethylene from components lighter than ethylene, and thus the ethylene product stream can have significant levels of components lighter than ethylene. In the case of steam cracking, therefore, this secondary ethylene product would contain undesirably high levels of both methane and hydrogen, rendering it unfit for use in most ethylene conversion processes, such as the manufacture of polyethylene.

Surprisingly, we have found that making a rough separation of methane and hydrogen downstream of the ethylene distributor and upstream of the hydrogen recovery and purification section of the plant significantly increases the hydrogen recovery of the process with only a small increase in energy levels. In contrast to standard distributed distillation systems, a hydrogen depleted gas is expanded and used for refrigeration, so less hydrogen is degraded from chemical to fuel value. This overcomes one of the disadvantages of prior art ethylene recovery systems based on an ethylene distributor, namely, low hydrogen recovery. We have further found that the methane rich gas from the aforesaid rough separation can be expanded and chilled to provide a cooling duty to the overall process.

SUMMARY OF THE INVENTION

The present invention is a process for the recovery of ethylene from a gas mixture comprising ethylene, ethane, acetylene, methane, hydrogen, and components heavier than ethane, comprising: a) directing the gas mixture to a first distillation column and recovering therefrom a first vapor overhead stream comprising ethane, ethylene, acetylene, hydrogen and methane and a first bottoms stream comprising components heavier than ethane; b) removing acetylene from the first vapor overhead stream to produce a low-acetylene first overhead stream; c) directing at least a portion of the low-acetylene first overhead stream to an ethylene distributor distillation column and recovering therefrom an ethylene distributor vapor overhead stream comprising ethylene, methane and hydrogen and substantially free of ethane, and an ethylene distributor bottoms stream comprising ethylene and ethane; d) separating the ethylene distributor overhead vapor stream into a light stream enriched in hydrogen and one or more streams depleted in hydrogen and comprising ethylene, said separation comprising at least one step of chilling at least a portion of the ethylene distributor overhead vapor stream; e) directing at least a portion of at least one of the one or more streams depleted in hydrogen to a demethanizer distillation column and withdrawing therefrom a demethanizer overhead stream comprising methane and hydrogen and substantially free of ethylene (for example, containing less than about 1 mole percent of ethylene) and a demethanizer bottoms stream comprising purified ethylene; and f) recovering a purified ethylene product from the ethylene distributor bottoms steam.

The present invention is also a process for the recovery of ethylene from a gas mixture comprising ethylene, ethane, acetylene, methane, hydrogen, C3 components, and components heavier than propane, comprising: a) directing the gas mixture to a first distillation column and recovering therefrom a first vapor overhead stream comprising ethane, ethylene, acetylene, hydrogen, methane, and C3 components, and a first bottoms stream comprising components heavier than propane and optionally C3 components; b) removing acetylene from the first vapor overhead stream to produce a low-acetylene first overhead stream; c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; d) separating the ethane-free vapor stream of step (c) into a light stream enriched in hydrogen and one or more streams depleted in hydrogen and comprising ethylene, said separation comprising at least one step of chilling at least a portion of the ethane-free vapor stream; e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; and f) recovering a second purified ethylene product from the C2s distributor and ethylene distributor bottoms streams.

BRIEF DESCRIPTION OF THE DRAWINGS

For a more complete understanding of this invention, reference should now be made to the embodiments illustrated in greater detail in the accompanying drawings and described below by way of examples of the invention.

Figure 1:
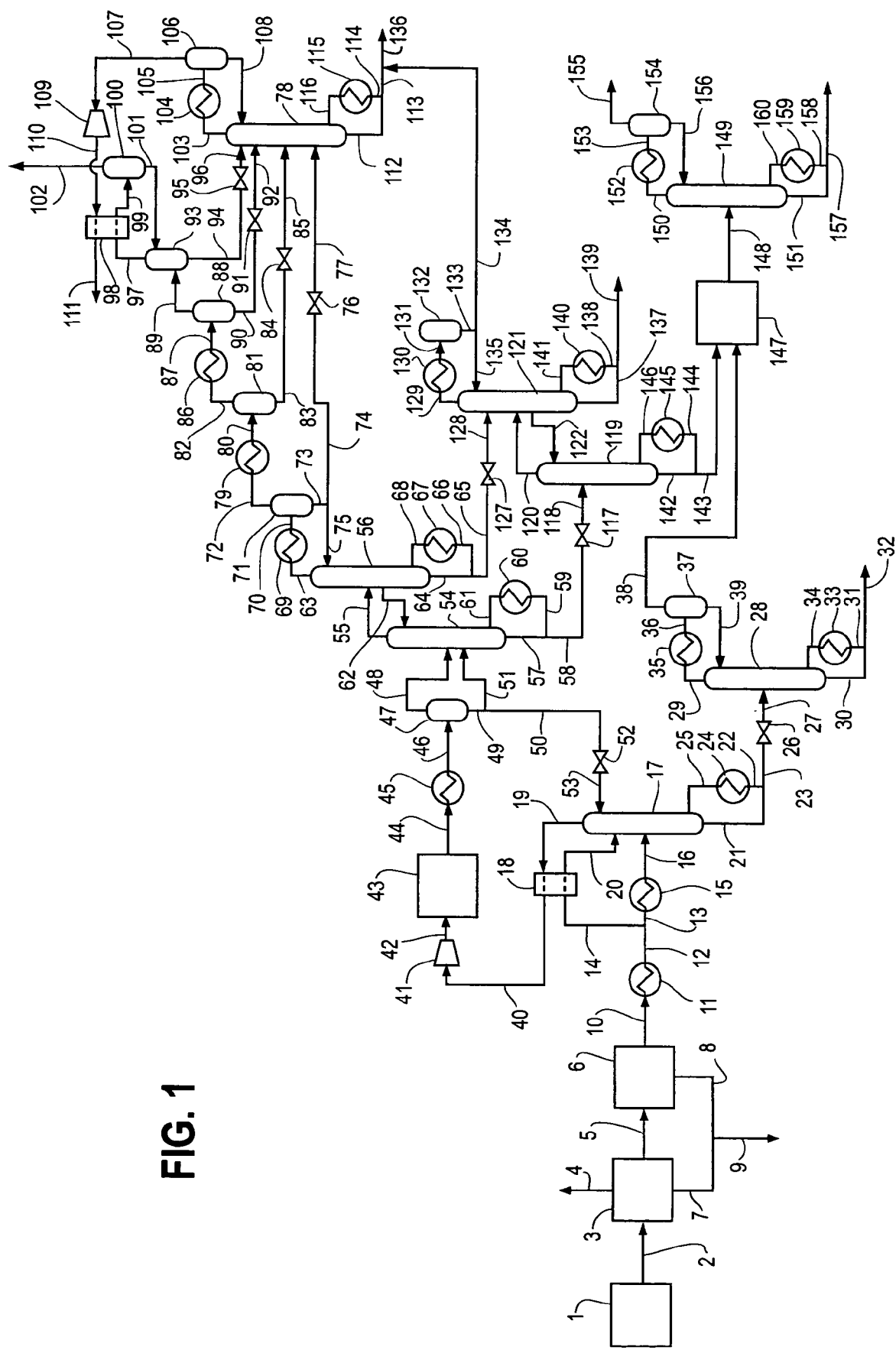
FIG. 1 is a schematic illustration of a preferred embodiment of the method of this invention.

It should be remembered that the drawings are not to scale and are schematic in nature. In certain instances, details which are not necessary for an understanding of the present invention or which renders other details difficult to perceive may be omitted. It should be understood, of course, that the invention is not necessarily limited to the particular embodiments illustrated herein.

DETAILED DESCRIPTION OF THE INVENTION

It should be recognized that the present invention can be employed for recovering and purifying ethylene and optionally propylene in a large variety of processes even through it is described herein in the context of treating the effluent from a stream cracking furnace. This invention can also be employed to a wide range of feeds and mixtures of feeds.

The present invention comprises steps (a)-(f) and is a process for the recovery of ethylene from a gas mixture comprising ethylene, ethane, acetylene, methane, hydrogen, and components heavier than ethane. Step (a) of the method of this invention comprises directing the gas mixture to a first distillation column and recovering therefrom a first vapor overhead stream comprising ethane, ethylene, acetylene, hydrogen and methane and a first liquid bottoms stream comprising components heavier than ethane. In one embodiment of step (a), the first distillation column is a deethanizer, and the first vapor overhead stream is substantially free of components heavier than ethane. In another embodiment of step (a), the first distillation column is a depropanizer, and the first vapor overhead stream contains is substantially free of components heavier than propane. In a preferred embodiment of step (a), the gas mixture is split into at least two fractions, the first of which is brought into indirect heat exchange contact with the first vapor overhead stream to thereby cool such first fraction and warm the first overhead vapor stream, and the second or more of which are introduced into the first distillation column at different locations.

Step (b) of the method of this invention comprises removing acetylene from the first vapor overhead stream to produce a low-acetylene first overhead stream. In one embodiment of step (b), the step of removing acetylene comprises the hydrogenation of acetylene to ethylene or ethane or both. Preferably step (b) comprises reacting acetylene and hydrogen contained in the first overhead stream in the presence of a suitable catalyst to form acetylene hydrogenation products. The first vapor overhead stream can be compressed before acetylene is removed therefrom.

Step (c) of the method of this invention comprises directing at least a portion of the low-acetylene first overhead stream to an ethylene distributor distillation column and recovering therefrom an ethylene distributor overhead stream comprising ethylene, methane and hydrogen and substantially free of ethane, and an ethylene distributor bottom stream comprising ethylene and ethane. In the context of this invention, an ethylene-containing stream is said to be "ethane-free" or "substantially free of ethane" when no further separation of the ethane and ethylene is necessary in order to produce a product-quality ethylene stream. In such a stream, the molar ratio of ethane to ethylene will typically be below about 0.005, though in some cases a higher ratio could be tolerated. In one embodiment at least a portion of the reflux liquid for the first distillation column is provided by a liquid side draw stream from the ethylene distributor distillation column. In another embodiment, at least one feed to the ethylene distributor distillation column comprises the overhead vapor of an upstream distillation column, and a liquid side draw is taken from the ethylene distributor distillation column and directed as reflux liquid to such upstream column, which serves as a C2s distributor column or the first distillation column. The ethylene distributor column is downstream of the first distillation column. The ethylene distributor distillation column operates with a top pressure preferably between 150 psig and 550 psig, more preferably between 150 psig and 450 psig.

In another preferred embodiment, step (c) comprises steps (g)-(m), of which step (g) comprises withdrawing a vapor stream comprising ethylene, methane, and hydrogen from the ethylene distributor distillation column; step (h) comprises chilling said vapor stream of step (g) to a temperature no colder than −50° F. to produce a partially condensed vapor stream; step (i) comprises directing the partially condensed vapor stream of step (h) to the bottom of a rectification means; step (j) comprises withdrawing an overhead vapor from the rectification means; step (k) comprises further chilling the overhead vapor from the rectification means to produce a partially condensed rectification means overhead stream; step (l) comprises directing at least a portion of the liquid fraction of the partially condensed rectification means overhead stream to the top of the rectification means as reflux liquid; and step (m) comprises withdrawing the vapor portion of the partially condensed rectification means overhead stream as the ethylene distributor vapor overhead stream. The rectification means can be an upper section of the ethylene distributor or a separate column or pressure shell downstream of the ethylene distributor.

Step (d) of the method of the present invention comprises separating the ethylene distributor overhead vapor stream into a light stream enriched in hydrogen and one or more steams depleted in hydrogen and comprising ethylene, such separation comprising at least one step of chilling at least a portion of the ethylene distributor overhead vapor stream. In a preferred embodiment, step (d) comprises steps (g), (h) and (i), wherein step (g) comprises chilling and partially condensing at least a portion of the ethylene distributor overhead stream; step (h) comprises separating the vapor and liquid contained in the partially condensed portion of the ethylene distributor overhead vapor, such separated liquid comprising one of the one or more liquid streams depleted in hydrogen and comprising ethylene; and step (i) comprises recovering the vapor stream enriched in hydrogen from the separated vapor of step (h). More preferably at least a portion of the separated vapor of step (h) is subjected to rectification in a methane rectification column, and an overhead vapor stream comprising the vapor stream enriched in hydrogen is withdrawn from the methane rectification column. In another embodiment, step (d) comprises rectification of at least a portion of the ethylene distributor overhead stream in a rectification column and withdrawing from the rectification column an overhead vapor stream comprising the vapor stream enriched in hydrogen.

Step (e) of the method of this invention comprises directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene. Preferably the demethanizer distillation column is operated at pressure that is at least 25 psi lower than that at which the ethylene distributor distillation column is operated.

Step (f) of the method of this invention comprises recovering a purified ethylene product from the ethylene distributor bottoms stream. Preferably step (f) comprises directing the ethylene distributor bottoms stream to a C2 splitter distillation column and withdrawing from an upper section of the C2 splitter distillation column a second purified ethylene product. More preferably, the second purified ethylene product is a liquid withdrawn from a tray that is at least one tray below the top of the C2 splitter distillation column, and a portion of the overhead vapor stream from the top of the C2 splitter distillation column is directed to a location that is at least one tray above the bottom of the demethanizer distillation column.

In the method of this invention, at least a portion of the stripping vapor of the first distillation column, the ethylene distributor distillation column, and the demethanizer distillation column is provided by vaporization of at least a part of the respective column bottoms liquid streams in a reboiler exchanger. Preferably, a refrigeration system containing more than one component in the working fluid is employed to provide at least a portion of the overhead condensing duty for each of the ethylene distributor distillation column and the demethanizer distillation column and at least a portion of the chilling duty required for the separation in step (d).

In another embodiment of the process of this invention of aforesaid steps (a)-(f), aforesaid steps (g)-(i) and aforesaid steps (g)-(m), the initial gas mixture also contains C3 components and components heavier than propane, and the first vapor overhead stream is substantially free of components heavier than ethane, and the first bottoms stream comprise C3 components and components heavier than propane.

In yet another embodiment, the present invention is a process for recovery of ethylene from a gas mixture comprising ethylene, ethane, acetylene, methane, hydrogen, C3 components and components heavier than propane and comprises steps (a)-(f). Step (a) of this embodiment comprises directing the gas mixture to a first distillation column and recovering therefrom a first vapor overhead stream comprising ethane, ethylene, acetylene, hydrogen, methane and C3 components and a first liquid bottoms stream comprising components heavier than propane and optionally C3 components and substantially free of C2 components. In a preferred embodiment of step (a), the first distillation column is a depropanizer, and the first vapor overhead stream is substantially free of components heavier than propane. In a preferred embodiment of step (a), the gas mixture is split into at least two fractions, the first of which is brought into indirect heat exchange contact with the first vapor overhead stream to thereby cool such first fraction and warm the first overhead vapor stream, and the second or more of which are introduced into the first distillation column at different locations.

Step (b) of the method of this invention comprises removing acetylene from the first vapor overhead stream to produce a low-acetylene first overhead stream. In one embodiment of step (b), the step of removing acetylene comprises the hydrogenation of acetylene to ethylene or ethane or both. Preferably step (b) comprises reacting acetylene and hydrogen contained in the first overhead stream in the presence of a suitable catalyst to form acetylene hydrogenation products. The first vapor overhead stream can be compressed before acetylene is removed therefrom.

Step (c) of the method of this invention comprises separating at least a portion of the low-acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane.

A preferred embodiment of step (c) incorporates steps (g)-(k). In step (g) at least a portion of the low-acetylene first overhead stream is directed to a C2s distributor distillation column to recover therefrom a C2s distributor overhead stream comprising ethylene, ethane, methane and hydrogen and substantially free of components heavier than ethane, and a C2s distributor bottoms stream comprising ethylene, ethane, and components heavier than ethane. In step (h) the C2s distributor bottoms stream is withdrawn as the first liquid stream of step (c). In step (i) at least a portion of the C2s distributor overhead stream is directed to an ethylene distributor column to recover therefrom an ethylene distributor overhead stream comprising ethylene, methane, and hydrogen and substantially free of ethane and an ethylene distributor bottoms stream comprising ethylene and ethane. In step (j) the ethylene distributor overhead stream is withdrawn as the ethane-free vapor stream of step (c). In step (k) the ethylene distributor bottoms stream is withdrawn as the second liquid stream of step (c). In a more preferred embodiment, at least a portion of the reflux liquid to the C2s distributor column can be supplied by a liquid sidedraw taken from the ethylene distributor column.

Figure 2:
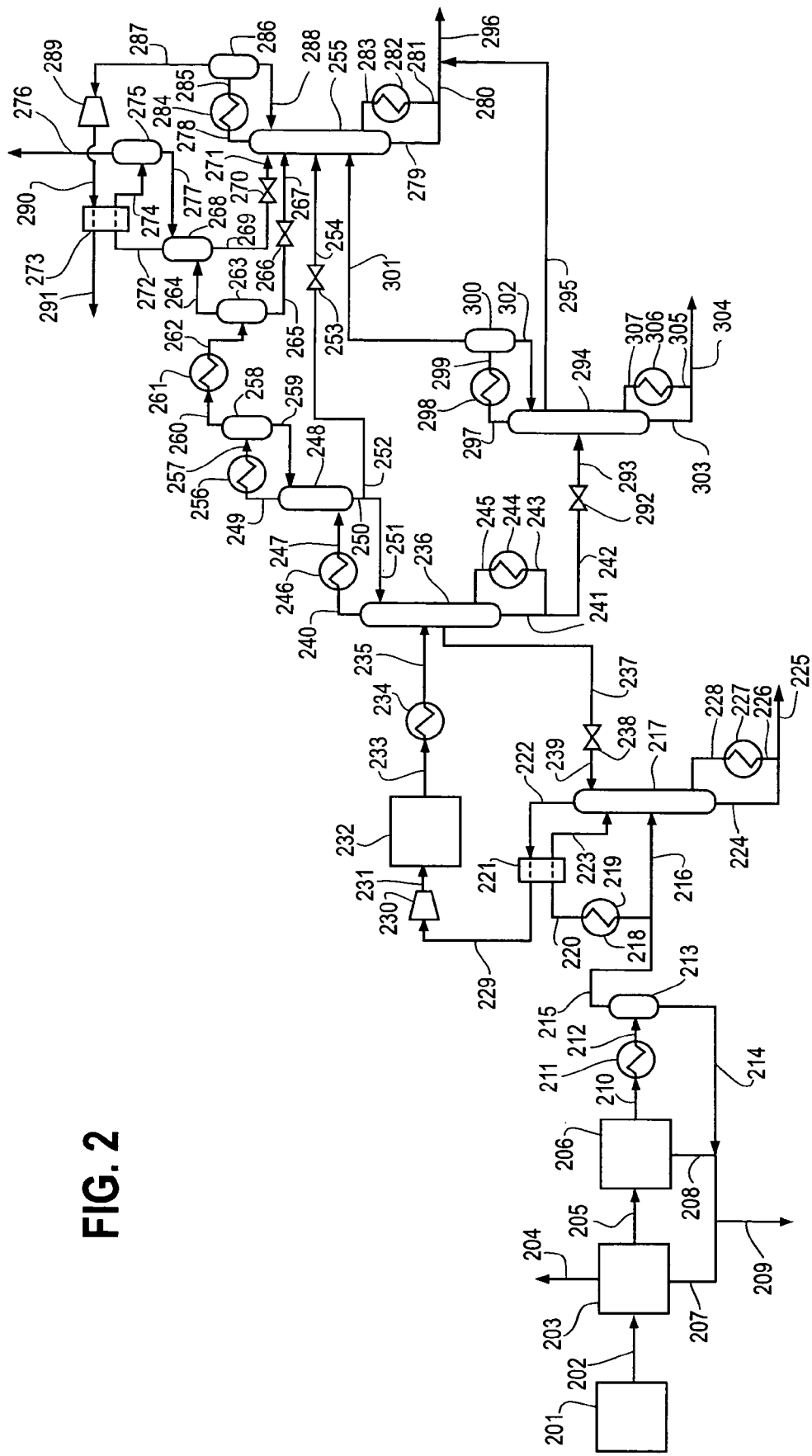
FIG. 2 is a schematic illustration of another preferred embodiment of the present invention.

Another preferred embodiment of step (c) which is not shown in FIGS. 1 and 2, comprises steps (g)-(m). In step (g) at least a portion of the low-acetylene first overhead stream is directed to an ethylene distributor distillation column to recover therefrom an ethylene distributor column overhead stream comprising ethylene, methane, and hydrogen and substantially free of ethane and an ethylene distributor column bottoms stream comprising ethylene, ethane and components heavier than ethane. In step (h) the ethylene distributor column overhead stream is withdrawn as the ethane-free vapor stream of step (c). In step (i) the ethylene distributor column bottoms stream is withdrawn as the first liquid stream of step (c). In step (j) a liquid sidedraw stream is withdrawn from the ethylene distributor column at a point intermediate between the top of the ethylene distributor column and the point where the low-acetylene first overhead stream enters the ethylene distributor column. The liquid sidedraw stream comprises methane, ethylene and ethane and is substantially free of components heavier than ethane. In step (k) the liquid sidedraw stream is directed to the top of a sidestripper column to recover therefrom a sidestripper bottoms stream comprising ethylene and ethane and substantially free of methane, and a sidestripper overhead stream comprising methane. In step (l) the sidestripper bottoms stream is withdrawn as the second liquid stream of step (c). In step (m) the sidestripper overhead stream is directed to the ethylene distributor column.

In a third preferred embodiment of step (c), which also is not shown in FIGS. 1 and 2, the separation functions of the ethylene distributor column and the sidestripper column described hereinabove are combined into a single divided wall column. The divided wall column produces an overhead product which is withdrawn as the ethane-free vapor stream of step (c) and two liquid bottoms products which are withdrawn as the first and second liquid streams of step (c). This embodiment of step (c) is disclosed in published U.S. patent application US 2004182751, which in its entirety is specifically incorporated herein by reference.

Step (d) of the method of the present invention comprises separating the ethane-free vapor stream of step (c) into a light stream enriched in hydrogen and one or more steams depleted in hydrogen and comprising ethylene, such separation comprising at least one step of chilling at least a portion of the ethane-free vapor stream. In a preferred embodiment, step (d) comprises steps (g), (h), and (i) wherein step (g) comprises chilling and partially condensing at least a portion of the ethane-free vapor stream, step (h) comprises separating the vapor and liquid contained in the partially condensed portion of the ethane-free vapor stream, such separated liquid comprising one of the one or more liquid streams depleted in hydrogen and comprising ethylene, and step (i) comprises recovering the vapor stream enriched in hydrogen from the separated vapor of step (h). More preferably at least a portion of the separated vapor of step (h) is subjected to rectification in a rectification column, and an overhead vapor stream comprising the vapor stream enriched in hydrogen is withdrawn from the rectification column. In another embodiment, step (d) comprises rectification of at least a portion of the ethane-free vapor stream from step (c) in a rectification column and withdrawing from the rectification column an overhead vapor stream comprising the vapor stream enriched in hydrogen.

Step (e) of the method of this invention comprises directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene. Preferably the demethanizer distillation column is operated at a pressure that is at least 25 psi lower than the pressure of the ethylene distributor column of step (c).

Step (f) of the method of this invention comprises recovering a purified ethylene product from the first and second liquid streams of step (c). Preferably step (f) comprises directing the second liquid stream to a C2 splitter distillation column and withdrawing from an upper section of the C2 splitter distillation column a second purified ethylene product. More preferably, the second purified ethylene product is a liquid withdrawn from a tray that is at least one tray below the top of the C2 splitter distillation column, and a portion of the overhead vapor stream from the top of the C2 splitter distillation column is directed to a location that is at least one tray above the bottom of the demethanizer distillation column. Preferrably, the C2 splitter distillation column is operated at a pressure at least 25 psi lower than that which exists at any location within any of the distillation columns used within step (c).

In another preferred embodiment, the second liquid stream of step (c) is directed to a C2 splitter distillation column to produce a C2 splitter bottoms stream comprising primarily ethane, and withdrawing from an upper section of the C2 splitter distillation column a second purified ethylene product. In another preferred embodiment, step (f) comprises directing the first liquid stream of step (c) to a deethanizer distillation column to produce a deethanizer overhead stream comprising primarily ethane and ethylene and a deethanizer bottoms stream comprising C3 components and components heavier than propane, and directing the deethanizer overhead stream to the C2 splitter distillation column. In this case, a purified propylene product can be recovered from the first bottoms stream and the deethanizer bottoms stream. Preferably at least a portion of the reflux liquid for the deethanizer distillation column is provided by a liquid side draw from the C2 splitter distillation column.

In the method of this invention, at least a portion of the stripping vapor to the first distillation column, each of the one or more distillation columns used within step (c), and the demethanizer distillation column is provided by vaporization of at least a part of the respective column bottoms liquid streams in a reboiler exchanger.

Preferably, a refrigeration system containing more than one component in the working fluid is employed to provide at least a portion of the overhead condensing duty for at least one of the distillation columns used in step (c) and the demethanizer distillation column, and at least a portion of the chilling duty required for the separation in step (d).

FIG. 1 depicts a first preferred embodiment of this invention which is particularly beneficial for recovering and purifying light olefins from the effluent of furnaces fed with relatively heavy hydrocarbons. In this embodiment the furnace feed is assumed to be a pure naphtha. As described in more detail above, the furnace section 1 produces a heated furnace effluent gas stream 2 which enters the quenching section 3 of the plant, where the hot furnace effluent is cooled, typically with water, to approximately ambient temperature and thereby producing high-pressure steam which is removed in line 4, and also providing heat for other parts of the process. The cooled furnace effluent gas stream 5 is fed to the compression section 6 where the pressure is increased in this embodiment to about 130 psig and again cooled to near ambient temperature. Any heavy liquids condensed in the quench section 3 and compression section 6 are withdrawn as streams 7 and 8, respectively, and combined in stream 9, which can be processed further if desired.

The higher-pressure effluent gas stream 10 is cooled against relatively warm refrigerant in exchanger 11 to produce stream 12. Stream 12 is split into two streams 13 and 14, stream 13 of which is further cooled in exchanger 15 to provide stream 16 which is fed to a lower portion of the partial depropanizer column 17. The other portion 14 of stream 12 is cooled in exchanger 18 by heat exchange against the overhead stream 19 from column 17 to provide stream 20 which is fed to an upper portion of column 17.

Column 17 acts as a partial depropanizer column which distributes hydrocarbons containing three carbon atoms into both the overheads and bottoms streams. Such a column is also known in the art as a C3s distributor column. The overhead vapor from column 17 in stream 19 contains propane, propylene, methylacetylene, propadiene, and components lighter than propylene. Stream 19 is substantially free of components heavier than propane, for example, containing less than about 0.1 mol % components heavier than propane. The bottoms product of column 17 in stream 21 contains C3 components and components heavier than propane, and is substantially free of components lighter than propylene, for example, containing less than about 0.1 mol % components lighter than propylene. Thus, the C3s distributor column 17 produces a sharp split between C2 and C4 components, and allows the C3 components to "distribute" between the overhead and bottoms streams. Optionally, column 17 could be operated as a full depropanizer column such that the column bottoms stream 21 is substantially free of C3 components, for example, containing less than about 0.1 mole percent C3 components. The scope of this invention covers the operation of column 17 as both a partial depropanizer and a full depropanizer. Stream 21 is split between streams 22 and 23. Stream 22 is heated and at least partially vaporized in reboiler exchanger 24 and the resulting stream 25 is returned as stripping vapor to column 17.

Stream 23 is reduced in pressure through valve 26, and the resulting stream 27 enters depropanizer column 28. Column 28 acts as a standard depropanizer tower, separating C3 components into the overhead stream 29 and C4 and heavier components into the bottoms stream 30. Stream 30 is split into streams 31 and 32. Stream 31 is heated and at least partially vaporized in reboiler exchanger 33, and the resulting stream 34 is returned as stripping vapor to column 28. Stream 32 may be processed elsewhere to purify or recover heavier components, if desired. Overhead stream 29 is cooled in exchanger 35, and the resulting stream 36 of liquid and gas is introduced into separation drum 37, with the gas removed as the overhead stream 38 and the liquid returned in stream 39 as reflux liquid to the top of column 28.

The overhead vapor of column 17, stream 19, is warmed in exchanger 18 and the resulting stream 40 enters the final stage of compression 41. The compressor effluent 42 enters a standard front-end acetylene hydrogenation system 43 which contains a number of exchangers and reactors, the detailed design options for which are well known to those skilled in the art. The location of the acetylene hydrogenation reaction is important because the acetylene must be removed from the cracked gas early in the process, such as in the "front end" hydrogenation system shown in FIG. 1. As is described hereinbelow, ethylene (and therefore any existing acetylene) will take multiple paths through the downstream separation section. It would be economically impractical to hydrogenate acetylene in the multiple ethylene streams that exist in the downstream separation section.

The effluent from the acetylene hydrogenation system, stream 44, is typically near ambient temperature. It is chilled and partially condensed in exchanger 45. In practice exchanger 45 would represent a number of exchangers in series which exchange heat between stream 44 and one or more refrigeration levels and/or sub-ambient temperature process streams. The vapor and liquid in partially condensed stream 46 are separated in drum 47. The vapor and liquid are withdrawn from drum 47 as streams 48 and 49, respectively. Liquid steam 49 is split into streams 50 and 51. The pressure of the liquid in stream 50 is reduced in valve 52, and the resulting stream 53 is returned as reflux to column 17. The remainder, if any, of the liquid from drum 47 in stream 51 is diverted to the C2s distributor column 54. The vapor from drum 47 in stream 48 is also directed to column 54. If desired, columns 56 and 17 can be thermally coupled. In this case drum 47 would be omitted, stream 46 would enter column 54 directly, and the reflux liquid stream 50 would be taken as a liquid sidedraw from column 54. This design is contained within the scope of this invention.

Column 54 acts as C2s distributor column. The overhead vapor of column 54, stream 55, contains ethane, ethylene and components lighter than ethylene and is directed to the ethylene distributor column 56. Column 54 is operated so that stream 55 is substantially free of C3 components, for example, containing less than about 1 mol % C3 components. The bottoms product of column 54, stream 57, contains ethylene, ethane, and components heavier than ethane, and is substantially free of components lighter than ethylene, for example, less than about 0.1 mol % components lighter than ethylene. Thus the C2s distributor column 54 produces a sharp split between C3 components and components lighter than ethylene, and allows ethane and ethylene to "distribute" between the overhead and bottoms streams. Stream 57 is split into streams 58 and 59, and stream 59 is heated and at least partially vaporized in reboiler exchanger 60 and the resulting stream 61 is returned as stripping vapor to column 54.

Preferably, columns 54 and 56 are thermally coupled in that reflux to column 54 is provided by stream 62, which is a liquid sidedraw from column 56. This thermal coupling between the C2s distributor column 54 and the ethylene distributor column 56 is beneficial in that it saves both energy and capital. If desired, the C2s distributor column 54 can be operated as a standard non-thermally coupled column with a partial condenser, though this mode of operation would be less energy efficient.

Column 56 acts as an ethylene distributor column. The net overhead vapor of column 56, stream 63, contains ethylene and components lighter than ethylene. The bottoms product of column 56, stream 64, contains primarily ethylene, ethane, and any components heavier than ethane that enter the column, and is substantially free of components lighter than ethylene, for example, containing less than about 0.1 mol % components lighter than ethylene. Column 56 is operated so that the overhead stream 63 is substantially free of ethane so that a purified ethylene product can be produced from stream 63 without requiring further separation of the ethane and ethylene contained in the stream. For example, the molar ratio of ethane to ethylene in stream 63 is typically less than about 0.005, preferably less than about 0.001. Thus, the ethylene distributor column 56 produces a sharp split between ethane and components lighter than ethylene, and allows ethylene to "distribute" between the overhead and bottoms streams. The bottoms stream 64 is split into streams 65 and 66, and stream 66 is heated and at least partially vaporized in reboiler exchanger 67 and the resulting stream 68 is returned as stripping vapor to column 56.

The vapor in stream 63 is cooled and partially condensed in exchanger 69 and the resulting liquid and vapor are fed in stream 70 to drum 71 where the liquid and vapor are separated as streams 72 and 73, respectively. The liquid is then split into streams 74 and 75, with the portion in stream 75 being returned to column 56 as reflux and with the remainder being directed in stream 74, through valve 76 and in stream 77, to demethanizer column 78.

Those skilled in the art will recognize that the combination of the thermally-coupled C2s distributor column 54 and ethylene distributor column 56 can be implemented in a number of ways. In addition to the separate thermally coupled columns shown in FIG. 1, other alternative implementations which are not shown are possible. One alternative implementation consists of an ethylene distributor column and thermally-coupled side stripper combination. In this implementation streams 48 and 51 enter the ethylene distributor column at an intermediate location, stream 63 is withdrawn from the top of the ethylene distributor column, and steam 57 is withdrawn from the bottom of the ethylene distributor column. A liquid sidestream is withdrawn from the ethylene distributor column at a point between where the feeds enter and the top of the column, and where the liquid within the column is substantially free of C3 components, for example, containing less than about 1 mol % C3 components. This liquid sidedraw is directed to the top of a sidestripper column in which the light gases, such as methane and hydrogen, are removed from the liquid. Stream 64 is withdrawn as the sidestripper bottoms, and the sidestripper overhead is directed back to the ethylene distributor column, to a point near where the liquid sidedraw was taken.

A second alternative implementation which is not shown combines the separation functions of the ethylene distributor and sidestripper columns described hereinabove into a single ethylene distributor divided wall column. Such an implementation has been taught in published U.S. patent application US 20044182751. In this case the dividing wall exists in a lower portion of the column and extends within the column from an intermediate point all the way to the bottom of the column. The dividing wall thereby provides for a single rectification section above the wall and for two separate half-sections in the lower portion of the column and on either side of the wall. The feed streams 48 and 51 enter one of the half-sections at a point below the top of the dividing wall. The section which the feed enters, along with the upper rectification section, make up the ethylene distributor column described hereinabove. The other half-section functions as the sidestripper column described hereinabove. Stream 63 is withdrawn from the top of the ethylene distributor divided wall column, stream 57 is withdrawn from the bottom of the ethylene distributor section, and stream 64 is withdrawn from the bottom of the sidestripper half-section. All of the possible column design options presented hereinabove for implementing the separations carried out by columns 54 and 56 of FIG. 1 are contained within the scope of this invention.

Columns 54 and 56 can operate over a relatively wide range of pressures. The optimal pressure for these columns will depend on a number of factors, including the type of refrigeration system used, the composition of the feeds entering the columns, the cost of energy, whether or not a purified hydrogen product is desired from the downstream separation section, and the required pressure of the purified hydrogen product that may be produced. Typically these columns will operate at a pressure between 150 psig and 550 psig, preferably within the range of 150 to 450 psig.

The vapor from drum 71, stream 72, is chilled and partially condensed in exchanger 79 from which the resulting liquid and vapor are passed in stream 80 to drum 81 where the liquid and vapor are separated. The vapor is withdrawn in stream 82 and the liquid is withdrawn in stream 83 and then passed through valve 84 and in stream 85 to column 78. The vapor in stream 82 is cooled in exchanger 86, and the resulting vapor and liquid are passed in stream 87 to drum 88 where the vapor and liquid are separated and withdrawn in streams 89 and 90, respectively, and the liquid then passes through valve 91 and stream 92 to column 78. The vapor in stream 89 is uncondensed gas from drum 88 and contains primarily hydrogen, methane and some ethylene.

Stream 89 is directed to methane rectifier column 93. This column contains a relatively small number of contact stages, typically less than ten theoretical stages. The purpose of this column is to separate ethylene from stream 89 and then recover the separated ethylene into the bottom stream 94 in an energy-efficient manner. The bottoms stream 94 contains primarily methane, ethylene, and dissolved hydrogen, and is directed through valve 95 and stream 96 to the demethanizer column 78. The overhead vapor from column 93 is withdrawn in stream 97 and enters exchanger 98 where it is partially condensed against a cold process or refrigerant stream. In the embodiment of FIG. 1, this cold process stream is the expanded demethanizer overhead vapor from column 78 and drum 106, as described hereinbelow. The vapor and liquid in the partially condensed stream 99 are separated in drum 100 and the liquid returned in stream 101 to column 93 as reflux. The hydrogen-rich vapor from drum 100, stream 102, contains primarily hydrogen and methane and relatively little ethylene. Stream 102 would typically be directed to a hydrogen recovery section, the design of which is well known to those skilled in the art.

It should be noted that other methods can be used to produce the hydrogen-rich stream 102 and the one or more methane-rich liquid streams (streams 83, 90 and 94) from the ethylene distributor column overhead vapor stream 72. FIG. 1 depicts two stages of partial condensation followed by a methane rectification step as one method. More or fewer partial condensation stages can be used. Also, other arrangements that combine one or more of the elements of process gas chilling, partial condensation, and rectification could also be used in place of the methane rectifier 93 in FIG. 1. For example, one or more dephlegmators, or the advanced rectification designs of U.S. Pat. Nos. 6,343,487 and 4,496,381 could be used, among others. These and other methods that can be utilized are all contained within the scope of this invention.

Column 78 acts as a demethanizer column, separating ethylene and any components heavier than ethylene from methane and lighter components. If the pressure of column 78 is lower than that of the chill train drums 71, 81 and 88 and the methane rectifier 93, the pressure of the various feed streams can be reduced through valves 76, 84, 91 and 95, respectively. Column 78 can operate over a relatively wide range of pressures. The optimal operating pressure of column 78 will depend on a number of factors, including the type of refrigeration system used, the composition of the feeds entering the columns, and the cost of energy, among others. Typically column 78 will operate at a pressure between 100 psig and 500 psig, preferably between 150 and 300 psig.

The overhead product of column 78 is withdrawn in stream 103, cooled and partially condensed in exchanger 104, and the resulting vapor and liquid are passed in stream 105 to drum 106 where the vapor and liquid are separated and withdrawn in streams 107 and 108, respectively. Stream 103 comprises methane and hydrogen and is substantially free of ethylene, for example, containing less than 1 mole percent of ethylene. The net overhead product of column 78, stream 107, contains primarily methane and hydrogen. It is sent to expander 109 to reduce the pressure and temperature of the stream. The resulting cooled, lower-pressure stream 110 can then be used to provide cooling for the process. FIG. 1 depicts one potential design where the expander effluent in stream 110 is used to provide chilling to the methane rectifier condenser 98. The resulting warmed expanded stream 111 typically is further warmed in other exchangers and used as fuel. Not shown, but if needed for heat balance, a portion of the hydrogen-rich stream 102 can be directed to the inlet of the expander 109 to provide additional cold expander outlet gas. The liquid stream 108 from drum 106 is returned to the top of the column 78 as reflux liquid. The bottoms product stream 112 from column 78 is split between streams 113 and 114, with stream 114 being heated and at least partially vaporized in reboiler exchanger 115 and the resulting stream 116 returned as stripping vapor to column 78. Stream 113 contains product-quality ethylene.

The embodiment of FIG. 1 requires external refrigeration to provide process cooling duties. In a typical ethylene plant the required refrigeration would be provided by cascaded propylene and ethylene refrigeration systems. We have found that the process of this invention provides maximum capital savings and energy reduction benefits when the refrigeration requirements are provided by a combination of a propylene refrigeration system for the warmer refrigeration levels, and a mixed refrigeration system for the colder levels. For the embodiment of FIG. 1, for example, propylene refrigerant could be utilized in exchangers 11, 15, 45, and 130 among others. The mixed refrigeration system would then provide at least a portion of the refrigeration for exchangers 69, 79, 86, and 104, among others. Those skilled in the art will recognize that there are many viable designs for a mixed refrigeration system that would provide the required duties. Likewise, there are many different mixed refrigerant compositions that could be used as the working fluid. Typically the mixed refrigerant would contain, but not be limited to, C1 to C3 hydrocarbons and additionally other light and heavy components to tailor the boiling behavior of the refrigerant mixture. All such details of the mixed refrigeration system design are within the scope of this invention.

Stream 58, a portion of the bottoms product of column 54, is directed through valve 117 and stream 118 to deethanizer column 119. Column 119 separates the C2 and lighter components from the C3 and heavier components. The overhead vapor from column 119 in stream 120 contains primarily ethane and ethylene and is substantially free of C3 components, for example less than 1 mol % C3 components. It is directed to the C2 splitter column 121. Preferably columns 119 and 121 are thermally coupled in that reflux to column 119 is provided by stream 122, a liquid sidedraw from column 121. This thermal coupling between the deethanizer and C2 splitter columns 119 and 121 is beneficial in that it saves both energy and capital. If desired, the deethanizer can be operated as a standard non-thermally coupled column with a partial or full condenser, though this mode of operation would be less energy efficient.

Column 121 is a C2 splitter column which separates ethylene and ethane into a purified ethylene top product and an ethane-rich bottoms product. It is fed with stream 120, the overhead product of column 119, and a portion of the bottoms product of column 56 passing through stream 65, valve 127 and stream 128. The overhead product of column 121, stream 129, is cooled and completely condensed in exchanger 130, and the resulting liquid stream 131 is introduced to drum 132 from which the liquid is withdrawn in stream 133 and then split between streams 134 and 135. Stream 134 contains product-quality ethylene. It is combined with stream 113 to provide the combined final ethylene product stream 136. Stream 135 is directed as reflux liquid to the top of column 121. The bottoms product from the C2 splitter column 121 is withdrawn in stream 137 and split between streams 138 and 139. Stream 138 is heated and at least partially vaporized in reboiler exchanger 140, and the resulting stream 141 is returned as stripping vapor to column 121. Stream 139 contains primarily ethane and is typically recycled to the furnace section 1.

Typically columns 119 and 121 would be operated at a pressure below that of columns 54 and 56. In this case, the pressure of streams 58 and 65 would be reduced through valves 117 and 127, respectively, or through some other pressure-reducing means. The optimal operating pressure of columns 119 and 121 will depend on a number of factors, including the type of refrigeration system used, the composition of the feeds entering the columns, and the cost of energy, among others. Typically these columns will operate at a pressure between 70 psig and 350 psig, preferably between about 150 and 300 psig.

The bottoms product of column 119 is withdrawn in stream 142 and split between streams 143 and 144. Stream 144 is heated and at least partially vaporized in reboiler exchanger 145, and the resulting stream 146 is returned as stripping vapor to column 119. Stream 143 contains primarily C3 components and is substantially free of C2 components, for example, containing less than 1 mol % C2 components. It is combined with stream 38 and directed to a methyl acetylene and propadiene (MAPD) hydrogenation system 147 as shown. The MAPD hydrogenation system effluent, stream 148, is directed to the C3 splitter tower 149 to produce an overhead product stream 150 and a bottoms product stream 151. Stream 150 is cooled and partially condensed in exchanger 152, and the resulting vapor and liquid stream 153 is introduced into drum 154 where the vapor and liquid are separated. The vapor is withdrawn in stream 155 which is product quality propylene. The liquid is withdrawn in stream 156 and returned as reflux to column 149. If desired, the overhead stream 150 can be completely condensed in exchanger 152 and the purified propylene product withdrawn as a liquid instead of a vapor. The bottoms product in stream 151 is split between stream 157 and 158. Stream 158 is heated and at least partially vaporized in exchanger 159, and the resulting stream 160 is returned as stripping vapor to column 149. Stream 157 contains primarily propane is typically recycled to the furnace section 1.

FIG. 2 depicts a second preferred embodiment of this invention which is particularly beneficial for recovering and purifying light olefins from the effluent of furnaces fed with relatively light hydrocarbons. The initial furnace, quench, and compression steps are similar to those described in the embodiment of FIG. 1. The respective stream compositions are typically somewhat different from those in FIG. 1, since the feed to the furnace section is different.

More particularly, the furnace section 201 produces a heated furnace effluent gas stream 202 which enters the quenching section 203 where the hot gas effluent is cooled, typically with water, to approximately ambient temperature and thereby producing high-pressure stream which is removed in line 204, and also providing heat for other parts of the process. The cooled effluent gas stream 205 is fed to the compression section 206 where the pressure is increased to about 170 psig and again cooled to near ambient temperature. Any heavy liquids condensed in the quench and compression sections are withdrawn as streams 207 and 208, respectively, and combined in stream 209 and can be pressured further, if desired. The higher-pressure effluent gas stream 210 is cooled and partially condensed against relatively warm refrigerant in exchanger 211, and the resulting vapor and liquid stream 212 is introduced into drum 213 where the vapor and liquid are separated to produce a relatively heavy liquid stream 214 and an uncondensed vapor stream 215. Liquid stream 214, can be combined with streams 207 and 208 in stream 209 as shown. Stream 215 is split into two streams. One is directed as stream 216 to a lower point on deethanizer column 217. The other portion in stream 218 is cooled in exchanger 219 and the resulting cooled stream 220 is cooled again in exchanger 221 against the overhead 222 from column 217. The resulting cooled stream 223 is directed to an upper point on column 217.

Column 217 acts as a front-end deethanizer column. The overhead stream 222 contains ethane, ethylene, and components lighter than ethylene and is substantially free of C3 components, for example, containing less than about 1 mol % C3 components. The bottoms stream 224 contains propylene, propane, and components heavier than propane and is substantially free of C2 components, for example, containing less than about 0.1 mol % C2 components. Stream 224 is split into streams 225 and 226, and stream 226 is heated and at least partially vaporized in reboiler exchanger 227, and the resulting stream 228 is returned to column 217 as stripping vapor. Stream 225 can be further processed to recover C3s or used as fuel, if desired. The overhead stream 222 is warmed in exchanger 221 and directed in stream 229 to the final stage of compression 230. The compressor effluent 231 enters a standard front-end acetylene hydrogenation system 232. This system contains a number of exchangers and reactors, for which the detailed design options are well known to those skilled in the art. As with the first embodiment of FIG. 1, any convenient conventional design of this acetylene hydrogenation system can be employed, and again the location of the acetylene hydrogenation reactor in the front end of the process is important.

The effluent from the acetylene hydrogenation system, stream 233, is typically near ambient temperature. It is chilled and partially condensed in exchanger 234. In practice exchanger 234 would represent a number of exchangers in series which exchange heat between stream 233 and one or more refrigeration levels and/or sub-ambient temperature process streams. The resulting chilled stream 235 enters the ethylene distributor column 236. From an energy and capital savings standpoint it is preferable that columns 217 and 236 are thermally coupled in that reflux liquid to column 217 is provided by a side draw liquid stream 237 from column 236 via valve 238 and stream 239. If desired, column 217 can also be operated in a non-coupled mode, similar in principle to column 17 in FIG. 1.

Column 236 operates as an ethylene distributor column. The gross overhead vapor stream 240 contains ethylene and components lighter than ethylene and is substantially free of ethane. For example, the molar ratio of ethane to ethylene in stream 240 is typically less than about 0.005, preferably less than about 0.001. The bottoms product stream 241 contains primarily ethylene and ethane and is substantially free of methane, for example, containing less than about 0.1 mol % methane. Stream 241 will also contain any components heavier than ethane that enter column 236. Stream 241 is split into streams 242 and 243. Stream 243 is heated and at least partially vaporized in reboiler exchanger 244 and the resulting stream 245 is returned as stripping vapor to column 236.

As one option of the present invention, column 236 operates with a reflux reheater section at the top. The gross overhead vapor of column 236, stream 240, contains primarily ethylene, methane and hydrogen. It is condensed as much as possible in exchanger 246 against relatively warm, for example, propylene-level refrigerant and optionally through the heating of sub-ambient temperature process streams. The temperature of the resulting partially condensed stream 247 leaving exchanger 246 will typically be in the range of −35 to −45° F. This stream 247 enters a reflux reheater column 248 which contains a relatively small number of contacting stages (typically less than 10 theoretical stages). The vapor and liquid in stream 247 disengage in the bottom of column 248. The vapor flows upward through the contacting stages and is cooled and partially rectified by downflowing cold liquid. The uncondensed vapor leaving the overhead of column 248, stream 249, is further chilled and partially condensed in exchanger 256. Refrigeration for exchanger 256 would typically be provided at least in part by a relatively cold refrigerant, for example, an ethylene or mixed refrigeration system. The vapor and liquid in stream 257 from exchanger 256 are separated in drum 258. The cold liquid in stream 259 from drum 258 enters the top of column 248 as reflux and is warmed and partially stripped of lighter components as it contacts the relatively warmer upflowing vapor. This reflux reheating arrangement for the top of the ethylene distributor column 236 reduces the energy required for refluxing the ethylene distributor by providing at least a part of it in exchanger 246 with propylene-range refrigerant. This arrangement also reduces the temperature of the vapor entering the ethylene or mixed refrigerant exchanger 256, thereby reducing the refrigeration requirement of this exchanger.

Those skilled in the art will recognize that the reflux reheater column 248 could be combined with the ethylene distributor column 236. In this case exchanger 246 would be a side condenser on the combined column, drawing vapor from the ethylene distributor trays below it and directing the partially condensed vapor to the reflux reheater rectification means situated above the ethylene distributor trays. Such a design is contained within the scope of this invention.

We have found that this reflux reheater arrangement can provide significant energy savings in the operation of the ethylene distributor, and is typically preferred if the operating pressure of the ethylene distributor column is relatively high, typically above about 400 psig, so that the gross overhead vapor can therefore be at least partially condensed in the propylene refrigeration range, that is, at temperatures greater than about −45° F. It is possible to operate column 236 at lower pressures, for example below about 400 psig, such that the gross overhead vapor cannot be at least partially condensed against propylene-range refrigeration. However, in this case the use of a reflux reheater configuration would be less advantageous. The optimal operating pressure of ethylene distributor column 236 will depend on a number of factors, including the type of refrigeration system used, the composition of the feed or feeds entering the column, the cost of energy, whether or not a purified hydrogen product is desired from the downstream separation section, and the required pressure of the purified hydrogen product that may be produced. Typically this column will operate at a pressure between 150 and 550 psig, preferably in the range of 150 to 450 psig.

The vapor from drum 258 is withdrawn through stream 260 which is cooled and partially condensed in exchanger 261. The resulting stream 262 of vapor and liquid is introduced into drum 263, where the vapor and liquid are separated and withdrawn as streams 264 and 265, respectively. The liquid stream 265 is directed through valve 266 and steam 267 to column 255.

The vapor from drum 263, stream 264, is directed to methane rectifier column 268. This column contains a relatively small number of contact stages, typically less than ten theoretical stages. The purpose of column 268 is to recover ethylene from stream 264 into the column bottoms stream 269 in an energy-efficient manner. The bottoms stream 269 contains primarily methane, ethylene, and dissolved hydrogen, and is directed through valve 270 and stream 271 to column 255. The overhead vapor in stream 272 from column 268 enters exchanger 273. It is cooled and partially condensed in exchanger 273 against a cold process or refrigerant stream. The vapor and liquid in the resulting partially condensed stream 274 are separated in drum 275, and the liquid returned to column 268 as reflux stream 277. The hydrogen-rich overhead vapor from drum 275, stream 276, contains primarily hydrogen and methane and relatively little ethylene. Stream 276 would typically be directed to a hydrogen recovery section, the design of which is well known to those skilled in the art.

As in the first embodiment, it should be noted that other methods can be used to produce the hydrogen-rich stream 276 and the one or more methane-rich liquid streams (streams 265 and 269 in FIG. 2) from the vapor stream 260. FIG. 2 depicts a single stage of partial condensation followed by a methane rectification step as one method. More or fewer partial condensation stages can be used. Also, other arrangements that combine one or more of the elements of process gas chilling, partial condensation, and rectification could also be used in place of the methane rectifier 268 in FIG. 2. For example, one or more dephlegmators, or the advanced rectification designs of U.S. Pat. Nos. 6,343,487 and 4,496,381 could be used, among others. These and other methods that can be utilized are all contained within the scope of this invention.

Column 255 acts as a demethanizer column, separating ethylene and any heavier components in the feeds from the methane and lighter components. If the pressure of column 255 is lower than that of the chill train drum 263 and columns 248 and 268, the pressure of the various feed streams can be reduced through valves 266, 253 and 270 as shown. Column 255 can operate over a relatively wide range of pressures. The optimal operating pressure of column 255 will depend on a number of factors, including the type of refrigeration system used, the composition of the feeds entering the columns, and the cost of energy, among others. Typically column 255 will operate at a pressure between 100 psig and 500 psig, preferably between 100 and 300 psig.

The overhead and bottoms products from column 255 are withdrawn through streams 278 and 279, respectively. Stream 279 is split into stream 280 and 281. Stream 281 is heated and at least partially vaporized in reboiler exchanger 282, and the resulting stream 283 is returned as stripping vapor to column 255. Stream 280 contains product-quality ethylene. The overhead stream 278 is cooled and partially condensed in exchanger 284, and the resulting cooled stream 285 is introduced into drum 286 where the vapor and liquid are separated. The vapor from drum 286, stream 287, contains primarily methane and hydrogen and is substantially free of ethylene. Stream 288 contains the liquid from drum 286 and is returned as reflux to column 255. Stream 287 is sent to expander 289 to reduce the pressure and temperature of the stream. This stream can then be used to provide cooling for the process. FIG. 2 depicts one potential design where the expander effluent in stream 290 is used to provide chilling to the methane rectifier condenser 273. The warmed expanded stream 291 is typically further warmed in other exchangers and can ultimately be used as fuel. Not shown, but if needed for heat balance, a portion of the hydrogen-rich stream 276 can be directed to the expander inlet to provide additional cold expander outlet gas.

Stream 242, a portion of the bottoms stream from the ethylene distributor column 236, is directed through valve 292 and stream 293 to the C2 splitter column 294. Column 294 acts to separate the ethane and ethylene contained in stream 293 to produce a purified ethylene product from the top section of the column and an ethane-rich bottoms product. Column 294 is typically operated at a pressure lower than column 236, so the pressure of stream 242 is reduced through valve 292 as shown. The C2 splitter column 294 typically operates at pressures between 150 psig and 350 psig.

In order to demonstrate an optional configuration included within the scope of this invention, column 294 operates with a pasteurizing section at its top. This section helps ensure that the ethylene product contains sufficiently low concentrations of methane or lighter gases. The liquid ethylene product, stream 295, is drawn from a tray a few stages from the top of column 294 and is combined with stream 280 to form the final ethylene product stream 296. The overhead product from column 294 is withdrawn in stream 297 which is cooled and partially condensed in exchanger 298, and the resulting cooled stream 299 is introduced into drum 300 where vapor and liquid are separated. A vapor vent stream, stream 301, can be taken from the C2 splitter reflux drum 300 and directed to a point near the bottom of the demethanizer column 255. Stream 301 contains primarily ethylene along with any light gases entering column 294 and will preferably enter a few stages above the bottom of column 255 so that any light gases contained in stream 301 are not carried into the purified ethylene product stream 280. A liquid stream 302 from the drum 300 is returned to column 294 as reflux. The bottoms product of column 294, stream 303, contains primarily ethane and is split into streams 304 and 305. Stream 304 is recovered and is typically recycled to the furnace section 201. Stream 305 is heated and at least partially vaporized in reboiler exchanger 306. The resulting stream 307 is returned as stripping vapor to column 294.

The following specific example serves to illustrate certain specific embodiments of the invention disclosed herein. This example is for illustrative purposes and should not be construed as limiting the scope of the invention disclosed herein as there are many alternative modifications and variations which will be apparent to those skilled in the art and which fall within the scope and spirit of the disclosed invention.

EXAMPLE

An example of the second embodiment of this invention was simulated using a commercially available simulation package. The process simulated in the example is identical to the preferred embodiment of FIG. 2. The feed to the furnace in this example was approximately 345,000 pounds per hour of a mixture of 70 weight percent of ethane and 30 weight percent of propane. The cracked gas was initially compressed to 172 psig and cooled to 59° F. against propylene refrigerant in exchanger 211. The flow rates and compositions of key streams in FIG. 2 are given in Table 1, and the key heat exchanger duties are given in Table 2.

The specific energy for the process of this example is determined to be 5,100 BTU/lb of ethylene. This is substantially lower than the specific energy of other commercially available processes, which average approximately 5,700 BTU/lb for ethane cracking, as reported in *Hydrocarbon Processing*, March 2003, pp. 96-98. It is clear that the energy performance of the process of this invention represents a significant energy savings relative to current practice.

From the above description, it is apparent that the objects of the present invention have been achieved. While only certain embodiments have been set forth, alternative embodiments and various modifications will be apparent form the above description to those skilled in the art. These and other alternatives are considered equivalents and are within the spirit and scope of the present invention.

TABLE 1

Flows and Conditions for Streams of The Example

| | Stream No. | | | | | | | |
| --- | --- | --- | --- | --- | --- | --- | --- | --- |
| | 215 | 216 | 222 | 223 | 225 | 235 | 237 | 242 |
| Temperature (F.) | 59.2 | 58.6 | −65.1 | −54.0 | 149.8 | 5.0 | −5.2 | 42.6 |
| Pressure (psig) | 172 | 170 | 165 | 170 | 168 | 514 | 511 | 515 |
| Vapor Fraction | 1.00 | 1.00 | 1.00 | 0.96 | 0.00 | 1.00 | 0.00 | 0.00 |

TABLE 1-continued

Flows and Conditions for Streams of The Example

Molar flows (lb mol/hr)

| | | | | | | | | |
|---|---|---|---|---|---|---|---|---|
| CO | 36.4 | 9.1 | 37.3 | 27.3 | 0.0 | 37.3 | 0.8 | 0.0 |
| HYDROGEN | 22084.8 | 5521.2 | 22317.4 | 16563.6 | 0.0 | 22028.4 | 232.6 | 0.0 |
| METHANE | 24779.4 | 6194.9 | 26232.3 | 18584.6 | 0.0 | 26232.3 | 1452.9 | 16.0 |
| ETHYLENE | 262439.0 | 65609.7 | 327395.6 | 196829.2 | 0.2 | 327880.5 | 64956.9 | 139973.0 |
| ETHANE | 163527.0 | 40881.8 | 231829.1 | 122645.3 | 5.7 | 233724.3 | 68307.7 | 165382.8 |
| ACETYLENE | 2091.2 | 522.8 | 2091.2 | 1568.4 | 0.0 | 0.0 | 0.0 | 0.0 |
| PROPYLENE | 8054.8 | 2013.7 | 100.0 | 6041.1 | 7981.1 | 100.0 | 26.3 | 73.7 |
| PROPANE | 1052.6 | 263.1 | 0.0 | 789.4 | 1052.6 | 0.0 | 0.0 | 0.0 |
| PROPDIENE | 47.0 | 11.7 | 0.0 | 35.2 | 47.0 | 0.0 | 0.0 | 0.0 |
| METHYLACETYLENE | 87.2 | 21.8 | 0.0 | 65.4 | 87.2 | 0.0 | 0.0 | 0.0 |
| ISOBUTANE | 2.1 | 0.5 | 0.0 | 1.6 | 2.1 | 0.0 | 0.0 | 0.0 |
| ISOBUTENE | 19.3 | 4.8 | 0.0 | 14.5 | 19.3 | 0.0 | 0.0 | 0.0 |
| 1,3 BUTADIENE | 7293.0 | 1823.3 | 0.0 | 5469.8 | 7293.0 | 0.0 | 0.0 | 0.0 |
| BUTENE-1 | 675.5 | 168.9 | 0.0 | 506.6 | 675.5 | 0.0 | 0.0 | 0.0 |
| N BUTANE | 988.2 | 247.0 | 0.0 | 741.1 | 988.2 | 0.0 | 0.0 | 0.0 |
| T-BUTENE 2 | 205.3 | 51.3 | 0.0 | 154.0 | 205.3 | 0.0 | 0.0 | 0.0 |
| C-BUTENE 2 | 136.8 | 34.2 | 0.0 | 102.6 | 136.8 | 0.0 | 0.0 | 0.0 |
| C5+ | 175.1 | 43.8 | 0.0 | 131.3 | 175.1 | 0.0 | 0.0 | 0.0 |
| Total | 493694.5 | 123423.6 | 610002.8 | 370270.9 | 18668.9 | 610002.8 | 134977.2 | 305445.5 |

| | Stream No. | | | | | | | | |
|---|---|---|---|---|---|---|---|---|---|
| | 260 | 264 | 265 | 269 | 280 | 287 | 295 | 301 | 304 |
| Temperature (Deg F.) | −79.3 | −168.0 | −168.0 | −168.0 | −40.4 | −186.0 | −32.1 | −33.6 | 9.6 |
| Pressure (psig) | 500 | 498 | 498 | 498 | 195 | 498 | 225 | 220 | 240 |
| Vapor Fraction | 1.00 | 1.00 | 0.00 | 0.00 | 0.00 | 1.00 | 0.00 | 1.00 | 0.00 |

Molar flows (lb mol/hr)

| | | | | | | | | | |
|---|---|---|---|---|---|---|---|---|---|
| CO | 36.4 | 33.1 | 3.3 | 0.3 | 0.0 | 3.6 | 0.0 | 0.0 | 0.0 |
| HYDROGEN | 21795.8 | 21597.2 | 198.6 | 15.6 | 0.0 | 214.2 | 0.0 | 0.0 | 0.0 |
| METHANE | 24763.4 | 16321.9 | 8441.5 | 662.4 | 3.9 | 9115.2 | 0.8 | 15.2 | 0.0 |
| ETHYLENE | 122950.4 | 9252.0 | 113698.5 | 8923.0 | 137587.4 | 19.0 | 124213.6 | 14983.9 | 775.4 |
| ETHANE | 32.9 | 1.2 | 31.7 | 1.2 | 33.8 | 0.0 | 33.3 | 0.9 | 165348.6 |
| ACETYLENE | 0.0 | 0.0 | 0.0 | 0.0 | 0.0 | 0.0 | 0.0 | 0.0 | 0.0 |
| PROPYLENE | 0.0 | 0.0 | 0.0 | 0.0 | 0.0 | 0.0 | 0.0 | 0.0 | 73.7 |
| PROPANE | 0.0 | 0.0 | 0.0 | 0.0 | 0.0 | 0.0 | 0.0 | 0.0 | 0.0 |
| PROPDIENE | 0.0 | 0.0 | 0.0 | 0.0 | 0.0 | 0.0 | 0.0 | 0.0 | 0.0 |
| METHYLACETYLENE | 0.0 | 0.0 | 0.0 | 0.0 | 0.0 | 0.0 | 0.0 | 0.0 | 0.0 |
| ISOBUTANE | 0.0 | 0.0 | 0.0 | 0.0 | 0.0 | 0.0 | 0.0 | 0.0 | 0.0 |
| ISOBUTENE | 0.0 | 0.0 | 0.0 | 0.0 | 0.0 | 0.0 | 0.0 | 0.0 | 0.0 |
| 1,3 BUTADIENE | 0.0 | 0.0 | 0.0 | 0.0 | 0.0 | 0.0 | 0.0 | 0.0 | 0.0 |
| BUTENE-1 | 0.0 | 0.0 | 0.0 | 0.0 | 0.0 | 0.0 | 0.0 | 0.0 | 0.0 |
| N BUTANE | 0.0 | 0.0 | 0.0 | 0.0 | 0.0 | 0.0 | 0.0 | 0.0 | 0.0 |
| T-BUTENE 2 | 0.0 | 0.0 | 0.0 | 0.0 | 0.0 | 0.0 | 0.0 | 0.0 | 0.0 |
| C-BUTENE 2 | 0.0 | 0.0 | 0.0 | 0.0 | 0.0 | 0.0 | 0.0 | 0.0 | 0.0 |
| C5+ | 0.0 | 0.0 | 0.0 | 0.0 | 0.0 | 0.0 | 0.0 | 0.0 | 0.0 |
| Total | 169579.1 | 47205.4 | 122373.7 | 9602.5 | 137625.1 | 9352.0 | 124247.7 | 15000.0 | 166197.8 |

TABLE 2

Heat Exchanger Duties

| Exchanger | Net Duty (MMBT U/hr) |
|---|---|
| 219 | −6.41 |
| 221 | −21.89 |
| 227 | 10.9 |
| 234 | −33.21 |
| 244 | 27.52 |
| 246 | −42.95 |
| 256 | −42.19 |
| 261 | −33.29 |
| 273 | −7.22 |
| 282 | 5.92 |
| 284 | −1.49 |
| 298 | −117.19 |
| 306 | 90.77 |

That which is claimed is:

1. A process for the recovery of ethylene from a gas mixture comprising ethylene, ethane, acetylene, methane, hydrogen, C3 components, and components heavier than propane, comprising: (a) directing the gas mixture to a first distillation column and recovering therefrom a first vapor overhead stream comprising ethane, ethylene, acetylene, hydrogen, methane, and C3 components, and a first bottoms stream comprising components heavier than propane and optionally C3 components; (b) removing acetylene from the first vapor overhead stream to produce a low-acetylene first overhead stream; (c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; (d) separating the ethane-free vapor stream of step (c), above, into a light stream enriched in hydrogen and one or more streams depleted in hydrogen and comprising ethylene, said separation comprising at least one step of chilling at least a portion of the ethane-free vapor stream of step (c), above; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a second purified ethylene product from the first and second liquid streams of step (c), above; (g) directing at least a portion, of step (c), above, of the low-acetylene first overhead stream to a C2s distributor distillation column and recovering therefrom a C2s distributor overhead stream comprising ethylene, ethane, methane and hydrogen and substantially free of components heavier than ethane, and a C2s distributor bottoms stream comprising ethylene, ethane, and components heavier than ethane and substantially free of components lighter than ethylene; (h) withdrawing the C2s distributor bottoms stream as the first liquid stream of step (c), above; (i) directing at least a portion of the C2s distributor overhead stream to an ethylene distributor column and recovering therefrom an ethylene distributor overhead stream comprising ethylene, methane, and hydrogen and substantially free of ethane and an ethylene distributor bottoms stream comprising ethylene and ethane and substantially free of components lighter than ethylene; (j) withdrawing the ethylene distributor overhead stream as the ethane-free vapor stream of step (c), above; and (k) withdrawing the ethylene distributor bottoms stream as the second liquid stream of step (c), above.

2. The process of claim 1 wherein the first vapor overhead stream is substantially free of components heavier than ethane.

3. The process of claim 1 wherein the first vapor overhead stream is substantially free of components heavier than propane.

4. The process of claim 1 wherein the step of removing acetylene comprises the hydrogenation of acetylene to ethylene or ethane or both.

5. The process of claim 1 wherein step (b) comprises reacting the acetylene and hydrogen contained in the first overhead stream in the presence of a suitable catalyst to form acetylene hydrogenation products.

6. The process of claim 1 wherein the first vapor overhead stream is compressed before entering the acetylene removal step (b).

7. The process of claim 1 wherein at least a portion of the reflux liquid for the first distillation column is provided by a liquid side draw stream from the ethylene distributor distillation column.

8. The Process of claim 1 wherein the ethylene distributor distillation column operates with a top pressure between 150 psig and 550 psig.

9. The Process of claim 1 wherein the ethylene distributor distillation column operates with a top pressure between 150 psig and 450 psig.

10. The process of claim 1 wherein step (d) comprises: g. chilling and partially condensing at least a portion of the ethylene distributor overhead stream to provide a partially condensed portion of the ethylene distributor overhead stream; h. separating the vapor and liquid contained in the partially condensed portion of the ethylene distributor overhead vapor, said separated liquid comprising one of the one or more liquid streams depleted in hydrogen and comprising ethylene; and i. recovering said vapor stream enriched in hydrogen from the separated vapor of step (h).

11. The process of claim 1 wherein at least a portion of the aforesaid separated vapor of step (h) is subjected to rectification in a rectification column and wherein an overhead vapor stream comprising the vapor stream enriched in hydrogen is withdrawn from the rectification column.

12. The process of claim 1 wherein step (d) comprises rectification of at least a portion of the ethylene distributor overhead stream in a rectification column and withdrawing from the rectification column an overhead vapor stream comprising the vapor stream enriched in hydrogen.

13. The process of claim 1 wherein the demethanizer distillation column is operated at a pressure at least 25 psi lower than that of the ethylene distributor distillation column.

14. The process of claim 1 wherein step (f) comprises directing at least a portion of the ethylene distributor bottoms stream to a C2 splitter distillation column and withdrawing from an upper section of the C2 splitter distillation column a purified ethylene product.

15. The process of claim 1 wherein at least a portion of the stripping vapor for the first distillation column, the ethylene distributor distillation column, and the demethanizer distillation column is provided by the vaporization of at least a part of the respective column bottoms liquid streams in a reboiler exchanger.

16. The process of claim 1 wherein a refrigeration system containing more than one component in the working fluid is used to provide at least a portion of the overhead condensing duty for the ethylene distributor distillation column, at least a portion of the overhead condensing duty of the demethanizer distillation column, and at least a portion of the chilling duty required for the separation of step (d).

17. The process of claim 1 wherein step (f) comprises directing the second liquid stream to a C2 splitter distillation column to produce a C2 splitter bottoms stream comprising primarily ethane, and withdrawing from an upper section of said C2 splitter distillation column the second purified ethylene product.

18. The process of claim 17 wherein step (f) further comprises directing the first liquid stream to a deethanizer distillation column to produce a deethanizer overhead stream comprising primarily ethane and ethylene and a deethanizer bottoms stream comprising C3 components and components heavier than propane, and directing said deethanizer overhead stream to said C2 splitter distillation column.

19. The process of claim 18 wherein a purified propylene product is recovered from the deethanizer bottoms stream and optionally from the first bottoms stream.

20. The process of claim 1 wherein the demethanizer distillation column is operated at a pressure at least 25 psi lower than the pressure of the ethylene distributor column of step (c).

21. The process of claim 1 wherein step (d) comprises: chilling and partially condensing at least a portion of the ethane-free vapor stream of step (c) to provide a partially condensed portion of the ethane-free vapor stream; separating the vapor and liquid contained in the partially condensed portion of the ethane-free vapor stream, said separated liquid comprising one of the one or more liquid streams depleted in hydrogen and comprising ethylene of step (d); and recovering said vapor stream enriched in hydrogen from the separated vapor.

22. The process of claim 21 wherein at least a portion of the aforesaid separated vapor is subjected to rectification in a rectification column and wherein an overhead vapor stream comprising the vapor stream enriched in hydrogen is withdrawn from the rectification column.

23. The process of claim 1 wherein step (d) comprises rectification of at least a portion of the ethane-free vapor from step (c) in a rectification column and withdrawing from the rectification column an overhead vapor stream comprising the vapor stream enriched in hydrogen.

24. A process for the recovery of ethylene from a gas mixture comprising ethylene, ethane, acetylene, methane, hydrogen, and optionally components heavier than ethane, comprising: (a) directing the gas mixture to a first distillation column and recovering therefrom a first vapor overhead stream comprising ethane, ethylene. acetylene, hydrogen and methane and a first bottoms stream comprising components heavier than ethane; (b) removing acetylene from the first vapor overhead stream to produce a low-acetylene first overhead stream; (c) directing at least a portion of the low-acetylene first overhead stream to an ethylene distributor distillation column and recovering therefrom an ethylene distributor vapor overhead stream comprising ethylene, methane and hydrogen and substantially free of ethane, and an ethylene distributor bottoms stream comprising ethylene and ethane; (d) separating the ethylene distributor overhead vapor stream into a light stream enriched in hydrogen and one or more streams depleted in hydrogen and comprising ethylene, said separation comprising at least one step of chilling at least a portion of the ethylene distributor overhead vapor stream; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a purified ethylene product from the ethylene distributor bottoms stream; and (g) splitting gas mixture into at least two fractions, one of said fractions is brought into indirect heat exchange contact with the first overhead vapor stream to warm the first overhead vapor stream and cool said fraction, and wherein the two or more fractions of said gas mixture are introduced into the first distillation column at different locations.

25. A process for the recovery of ethylene from a gas mixture comprising ethylene, ethane, acetylene, methane, hydrogen, and optionally components heavier than ethane, comprising: (a) directing the gas mixture to a first distillation column and recovering therefrom a first vapor overhead stream comprising ethane, ethylene, acetylene, hydrogen and methane and a first bottoms stream comprising components heavier than ethane; (b) removing acetylene from the first vapor overhead stream to produce a low-acetylene first overhead stream; (c) directing at least a portion of the low-acetylene first overhead stream to an ethylene distributor distillation column and recovering therefrom an ethylene distributor vapor overhead stream comprising ethylene, methane and hydrogen and substantially free of ethane, and an ethylene distributor bottoms stream comprising ethylene and ethane; (d) separating the ethylene distributor overhead vapor stream into a light stream enriched in hydrogen and one or more streams depleted in hydrogen and comprising ethylene, said separation comprising at least one step of chilling at least a portion of the ethylene distributor overhead vapor stream; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a purified ethylene product from the ethylene distributor bottoms stream; (g) withdrawing a vapor stream, in step (c), above, comprising ethylene, methane, and hydrogen from the ethylene distributor distillation column; (h) chilling said vapor stream of step (a), above, to a temperature no colder than −50 degree F. to produce a partially condensed vapor stream; (i) directing said partially condensed vapor stream of step (h), above, to the bottom of a rectification means; (j) withdrawing an overhead vapor from said rectification means; (k) chilling said overhead vapor from said rectification means to produce a partially condensed rectification means overhead stream; (l) directing at least a portion of the liquid fraction of said partially condensed rectification means overhead stream to the top of said rectification means as reflux liquid; and (m) withdrawing the vapor portion of said partially condensed rectification means overhead stream as said ethylene distributor vapor overhead stream.

26. A process for the recovery of ethylene from a gas mixture comprising ethylene, ethane, acetylene, methane, hydrogen, and optionally components heavier than ethane, comprising: (a) directing the gas mixture to a first distillation column and recovering therefrom a first vapor overhead stream comprising ethane, ethylene, acetylene, hydrogen and methane and a first bottoms stream comprising components heavier than ethane; (b) removing acetylene from the first vapor overhead stream to produce a low-acetylene first overhead stream; (c) directing at least a portion of the low-acetylene first overhead stream to an ethylene distributor distillation column and recovering therefrom an ethylene distributor vapor overhead stream comprising ethylene, methane and hydrogen and substantially free of ethane, and an ethylene distributor bottoms stream comprising ethylene and ethane; (d) separating the ethylene distributor overhead vapor stream into a light stream enriched in hydrogen and one or more streams depleted in hydrogen and comprising ethylene, said separation comprising at least one step of chilling at least a portion of the ethylene distributor overhead vapor stream; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a purified ethylene product from the ethylene distributor bottoms stream directing at least a portion of the ethylene distributor bottoms stream to a C2 splitter distillation column and withdrawing from an upper section of the C2 splitter distillation column a purified ethylene product; and (g) withdrawing said second purified ethylene product is a liquid from a tray at least one tray below the top of the C2 splitter distillation column, and a portion of the overhead vapor stream from the top of the C2 splitter distillation column is directed to a location at least one tray above the bottom of the demethanizer distillation column.

27. A process for the recovery of ethylene from a gas mixture comprising ethylene, ethane, acetylene, methane, hydrogen, C3 components, and components heavier than propane, comprising: (a) directing the gas mixture to a first distillation column and recovering therefrom a first vapor overhead stream comprising ethane, ethylene, acetylene, hydrogen, methane, and C3 components, and a first bottoms stream comprising components heavier than propane and optionally C3 components; (b) removing acetylene from the first vapor overhead stream to produce a low-acetylene first overhead stream; (c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; (d) separating the ethane-free vapor stream of step (C), above, into a light stream enriched in hydrogen and one or more streams depleted in hydrogen and comprising ethylene, said separation comprising at least one step of chilling at least a portion of the ethane-free vapor stream of step (c), above; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a second purified ethylene product from the first and second liquid streams of step (c), above; (g) directing, of step (c), above, at least a portion of the low-acetylene first overhead stream to an ethylene distributor distillation column and recovering therefrom an ethylene distributor column overhead stream comprising ethylene, methane, and hydrogen and substantially free of ethane and an ethylene distributor column bottoms stream comprising ethylene, ethane and components heavier than ethane and substantially free of components lighter than ethylene; (h) withdrawing the ethylene distributor column overhead stream as the ethane-free vapor stream of step (c), above; withdrawing the ethylene distributor column bottoms stream as the first liquid stream of step (c), above; (j) withdrawing a liquid sidedraw stream from the ethylene distributor column at a point intermediate between the top of the ethylene distributor column and the point where the low-acetylene first overhead stream enters the ethylene distributor column, wherein the liquid sidedraw stream comprises methane, ethylene and ethane and is substantially free of components heavier than ethane; (k) directing the liquid sidedraw stream to the top of a sidestripper column and recovering therefrom a sidestripper bottoms stream comprising ethylene and ethane and substantially free of components lighter than ethylene, and a sidestripper overhead stream comprising methane; (l) withdrawing the sidestripper bottoms stream as the second liquid stream of step (c), above; and (m) directing the sidestripper overhead stream to the ethylene distributor column.

28. A process for the recovery of ethylene from a gas mixture comprising ethylene, ethane, acetylene, methane, hydrogen, C3 components, and components heavier than propane, comprising: (a) directing the gas mixture to a first distillation column and recovering therefrom a first vapor overhead stream comprising ethane, ethylene, acetylene, hydrogen, methane, and C3 components, and a first bottoms stream comprising components heavier than propane and optionally C3 components; (b) removing acetylene from the first vapor overhead stream to produce a low-acetylene first overhead stream; (c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; (d) separating the ethane-free vapor stream of step (c), above, into a light stream enriched in hydrogen and one or more streams depleted in hydrogen and comprising ethylene, said separation comprising at least one step of chilling at least a portion of the ethane-free vapor stream of step (c), above; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a second purified ethylene product from the first and second liquid streams of step (c), above; (g) wherein step (c), above, comprises the steps of directing at least a portion of the low-acetylene first overhead stream to an ethylene distributor distillation column and recovering therefrom an ethylene distributor column overhead stream comprising ethylene, methane, and hydrogen and substantially free of ethane and an ethylene distributor column bottoms stream comprising ethylene, ethane and components heavier than ethane and substantially free of components lighter than ethylene; (h) withdrawing the ethylene distributor column overhead stream as the ethane-free vapor stream of step (c), above; (i) withdrawing the ethylene distributor column bottoms stream as the first liquid stream of step (c), above; (j) withdrawing a liquid sidedraw stream from the ethylene distributor column at a point intermediate between the top of the ethylene distributor column and the point where the low-acetylene first overhead stream enters the ethylene distributor column, wherein the liquid sidedraw stream comprises methane, ethylene and ethane and is substantially free of components heavier than ethane; (k) directing the liquid sidedraw stream to the top of a sidestripper column and recovering therefrom a sidestripper bottoms stream comprising ethylene and ethane and substantially free of components lighter than ethylene, and a sidestripper overhead stream comprising methane; (l) withdrawing the sidestripper bottoms stream as the second liquid stream of step (c), above; (m) directing the sidestripper overhead stream to the ethylene distributor column; and (n) combining the separation functions of the ethylene distributor column and the sidestripper column into a single divided wall column.

29. A process for the recovery of ethylene from a gas mixture comprising ethylene, ethane, acetylene, methane, hydrogen, C3 components, and components heavier than propane, comprising: (a) directing the gas mixture to a first distillation column and recovering therefrom a first vapor overhead stream comprising ethane, ethylene, acetylene, hydrogen, methane, and C3 components. and a first bottoms stream comprising components heavier than propane and optionally C3 components; (b) removing acetylene from the first vapor overhead stream to produce a low-acetylene first overhead stream; (c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; (d) separating the ethane-free vapor stream of step (c), above, into a light stream enriched in hydrogen and one or more streams depleted in hydrogen and comprising ethylene, said separation comprising at least one step of chilling at least a portion of the ethane-free vapor stream of step (c), above; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a second purified ethylene product from the first and second liquid streams of step (c), above; (g) wherein step (c), above, comprises the steps of directing at least a portion of the low-acetylene first overhead stream to an ethylene distributor distillation column and recovering therefrom an ethylene distributor column overhead stream comprising ethylene, methane, and hydrogen and substantially free of ethane and an ethylene distributor column bottoms stream comprising ethylene, ethane and components heavier than ethane and substantially free of components lighter than ethylene; (h) withdrawing the ethylene distributor column overhead stream as the ethane-free vapor stream of step (c), above; (i) withdrawing the ethylene distributor column bottoms stream as the first liquid stream of step (c), above; (j) withdrawing a liquid sidedraw stream from the ethylene distributor column at a point intermediate between the top of the ethylene distributor column and the point where the low-acetylene first overhead stream enters the ethylene distributor column, wherein the liquid sidedraw stream comprises methane, ethylene and ethane and is substantially free of components heavier than ethane; (k) directing the liquid sidedraw stream to the top of a sidestripper column and recovering therefrom a sidestripper bottoms stream comprising ethylene and ethane and substantially free of components lighter than ethylene, and a sidestripper overhead stream comprising methane; (l) withdrawing the sidestripper bottoms stream as the second liquid stream of step (c), above; (m) directing the sidestripper overhead stream to the ethylene distributor column; (n) combining the separation functions of the ethylene distributor column and the sidestripper column into a single divided wall column; and (o) producing an overhead product by the divided wall column and two distinct liquid bottoms products, and further wherein the overhead product is withdrawn as the ethane-free vapor stream of step (c), above, and the two bottoms products are withdrawn as the first and second liquid streams of step (c), above.

30. A process for the recovery of ethylene from a gas mixture comprising ethylene, ethane, acetylene, methane, hydrogen, C3 components, and components heavier than propane, comprising: (a) directing the gas mixture to a first distillation column and recovering therefrom a first vapor overhead stream comprising ethane, ethylene, acetylene, hydrogen, methane, and C3 components, and a first bottoms stream comprising components heavier than propane and optionally C3 components; (b) removing acetylene from the first vapor overhead stream to produce a low-acetylene first overhead stream; (c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; (d) separating the ethane-free vapor stream of step (c), above, into a light stream enriched in hydrogen and one or more streams depleted in hydrogen and comprising ethylene, said separation comprising at least one step of chilling at least a portion of the ethane-free vapor stream of step (c), above; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a second purified ethylene product from the first and second liquid streams of step (c), above wherein the second liquid stream is directed to a C2 splitter distillation column to produce a C2 splitter bottoms stream comprising primarily ethane, and withdrawing from an upper section of said C2 splitter distillation column the second purified ethylene product; (g) withdrawing said second purified ethylene product as a liquid from a tray at least one tray below the top of the C2 splitter distillation column, and a portion of the overhead vapor stream from the top of the C2 splitter distillation column is directed to a location at least one tray above the bottom of the demethanizer distillation column.

31. A process for the recovery of ethylene from a gas mixture comprising ethylene, ethane, acetylene, methane, hydrogen, C3 components, and components heavier than propane, comprising: (a) directing the gas mixture to a first distillation column and recovering therefrom a first vapor overhead stream comprising ethane, ethylene, acetylene, hydrogen, methane, and C3 components, and a first bottoms stream comprising components heavier than propane and optionally C3 components; (b) removing acetylene from the first vapor overhead stream to produce a low-acetylene first overhead stream; (c) separating at least a portion of the low acetylene first overhead stream through the use of one or more distillation columns, one of which acts as an ethylene distributor column, to recover an ethane-free vapor stream comprising ethylene, methane and hydrogen and substantially free of ethane, a first liquid stream comprising ethylene, ethane and components heavier than ethane, and a second liquid stream comprising ethylene and ethane and substantially free of components heavier than ethane; (d) separating the ethane-free vapor stream of step (c), above, into a light stream enriched in hydrogen and one or more streams depleted in hydrogen and comprising ethylene, said separation comprising at least one step of chilling at least a portion of the ethane-free vapor stream of step (c), above; (e) directing at least a portion of at least one of the one or more streams depleted in hydrogen to a demethanizer distillation column and withdrawing therefrom a demethanizer overhead stream comprising methane and hydrogen and substantially free of ethylene and a demethanizer bottoms stream comprising purified ethylene; (f) recovering a second purified ethylene product from the first and second liquid streams of step (c), above wherein the second liquid stream is directed to a C2 splitter distillation column to produce a C2 splitter bottoms stream comprising primarily ethane, and withdrawing from an upper section of said C2 splitter distillation column the second purified ethylene product; and (g) operating the C2 splitter distillation column at a pressure at least 25 psi lower than the pressure at any location in any of the distillation columns employed in step (c), above.

* * * * *